United States Patent
Schmid et al.

(10) Patent No.: US 7,037,188 B2
(45) Date of Patent: May 2, 2006

(54) SYSTEMS FOR DELIVERING CONDITIONED AIR TO PERSONAL BREATHING ZONES

(75) Inventors: William R. Schmid, Plymouth, MN (US); Dean W. Hacker, Fridley, MN (US); Eric J. Krause, Big Lake, MN (US)

(73) Assignee: Halo Innovations, Inc., Plymouth, MN (US)

( * ) Notice: Subject to any disclaimer, the term of this patent is extended or adjusted under 35 U.S.C. 154(b) by 0 days.

(21) Appl. No.: 10/820,083

(22) Filed: Apr. 6, 2004

(65) Prior Publication Data

US 2004/0242148 A1    Dec. 2, 2004

Related U.S. Application Data

(60) Provisional application No. 60/461,306, filed on Apr. 8, 2003, provisional application No. 60/539,360, filed on Jan. 27, 2004.

(51) Int. Cl.
*F24F 3/16*    (2006.01)

(52) U.S. Cl. .................. 454/187; 5/423; 55/385.1; 55/467; 55/467.1; 454/197; 454/230; 454/233

(58) Field of Classification Search ............. 454/187, 454/197, 230, 231, 233, 306; 5/423; 62/261; 55/385.1, 467, 467.1, 472, 473
See application file for complete search history.

(56) References Cited

U.S. PATENT DOCUMENTS

| | | | |
|---|---|---|---|
| 1,506,904 A * | 9/1924 | Harrison | ........... 454/306 |
| 3,101,488 A | 8/1963 | Peebles | |
| 3,151,929 A | 10/1964 | Potapenko | |
| 3,230,556 A | 1/1966 | Shippee | |
| 3,385,036 A | 5/1968 | Webb | |
| 3,462,920 A | 8/1969 | Denny | |
| 3,724,172 A | 4/1973 | Wood | |
| 3,795,092 A | 3/1974 | Schwartz et al. | |
| 3,820,536 A | 6/1974 | Anspach, Jr. et al. | |
| 3,838,556 A | 10/1974 | Finger | |
| 3,893,457 A | 7/1975 | van der Waaij | |
| 3,923,482 A | 12/1975 | Knab et al. | |

(Continued)

FOREIGN PATENT DOCUMENTS

DE    36 44 417 A1    7/1988

(Continued)

OTHER PUBLICATIONS

"Air Innovative Systems, Inc.—Clean Air with Mite-E-Air™," http:///www.webpaws.com/go2/AIS/, 1 page, Designed and Copyrighted © 1998-2003 (Printed Nov. 13, 2003).

(Continued)

Primary Examiner—Harold Joyce
(74) Attorney, Agent, or Firm—Hamre, Schumann, Mueller & Larson, P.C.

(57) ABSTRACT

A system to significantly improve the air quality in a personal breathing environment. The system includes a blower unit that produces a conditioned air flow, a delivery system that delivers air provided by the blower unit to a person's breathing zone, and a conduit that interconnects the blower unit and the delivery system for directing conditioned air from the blower unit to the delivery system. The delivery system is positioned so that it sends conditioned air around an individual's head and into the individual's personal breathing zone, thereby creating a zone of conditioned air around the individual's head.

5 Claims, 13 Drawing Sheets

U.S. PATENT DOCUMENTS

| | | | |
|---|---|---|---|
| 3,935,803 A | 2/1976 | Bush | |
| 4,023,472 A | 5/1977 | Grunder et al. | |
| 4,045,192 A | 8/1977 | Eckstein et al. | |
| 4,140,105 A | 2/1979 | Duvlis | |
| 5,129,928 A | 7/1992 | Chan et al. | |
| 5,160,517 A | 11/1992 | Hicks et al. | |
| 5,389,037 A | 2/1995 | Hale | |
| 5,832,919 A | 11/1998 | Kano et al. | |
| 5,943,716 A * | 8/1999 | Chu | 5/423 |
| 6,062,977 A | 5/2000 | Hague | |
| 6,099,607 A | 8/2000 | Haslebacher | |
| 6,119,689 A | 9/2000 | Korman | |
| 6,261,332 B1 | 7/2001 | Richard | |
| 2003/0033790 A1 | 2/2003 | Hague | |
| 2003/0150328 A1 | 8/2003 | Hansson et al. | |

FOREIGN PATENT DOCUMENTS

| | | |
|---|---|---|
| EP | 09010075 | 1/1997 |
| FR | 1448873 | 7/1966 |
| FR | 2594668 | 8/1987 |
| FR | 2833844 | 6/2003 |
| JP | 05141729 A | 6/1993 |
| JP | 07241318 A | 9/1995 |
| JP | 2000-116725 A | 4/2000 |
| JP | 2000-171067 A | 6/2000 |
| JP | 2002-031382 A | 1/2002 |

OTHER PUBLICATIONS

Villaveces, J. et al., "Use of Laminar Air Flow Portable Filter in Asthmatic Children," *Annals of Allergy*, vol. 38, pp. 400-404 (Jun. 1977).

Zwemer, R. et al., "Use of Laminar Control Devices as Adjunct to Standard Environmental Control Measures in Symptomatic Asthmatic Children," *Annals of Allergy*, vol. 31, pp. 284-290 (Jun. 1973).

\* cited by examiner

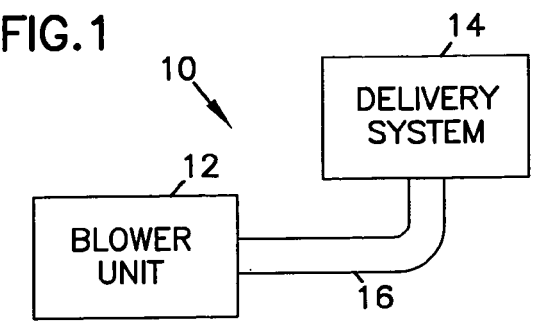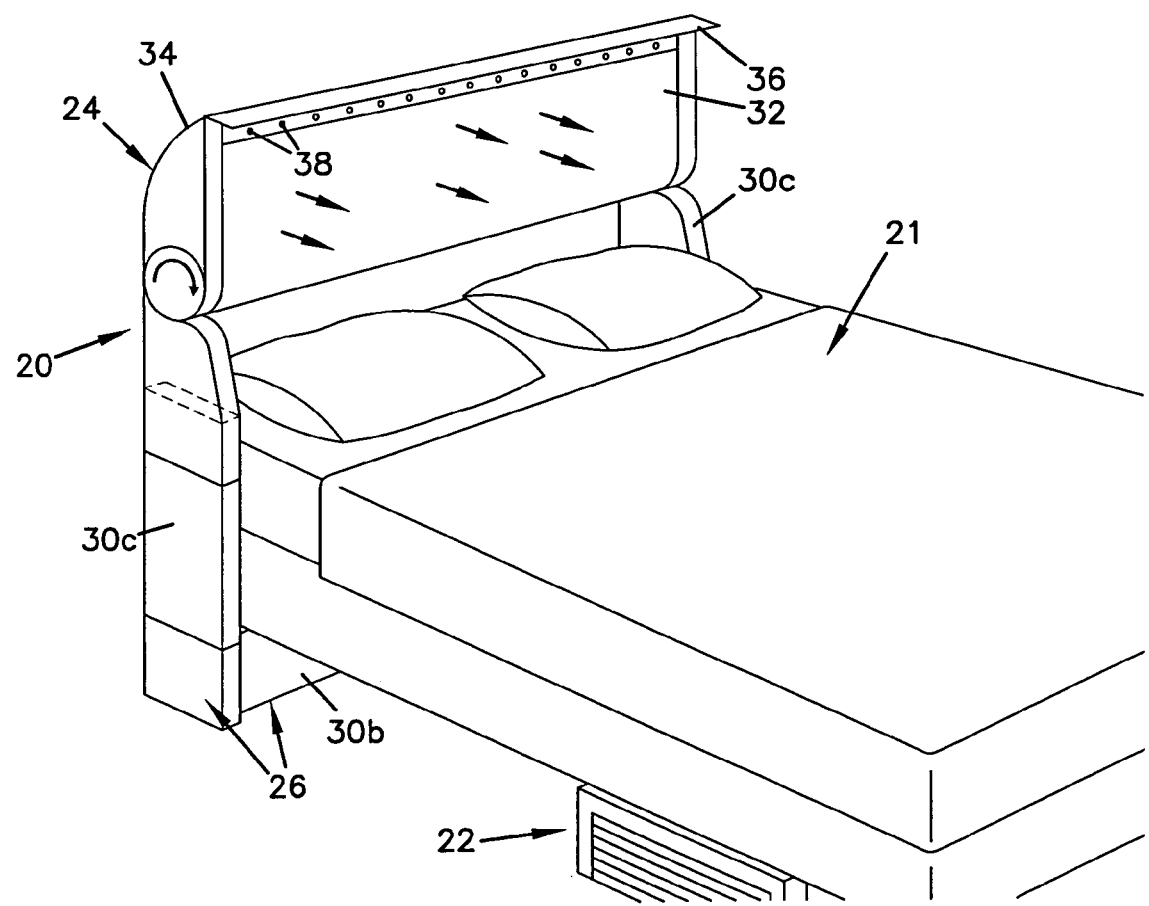

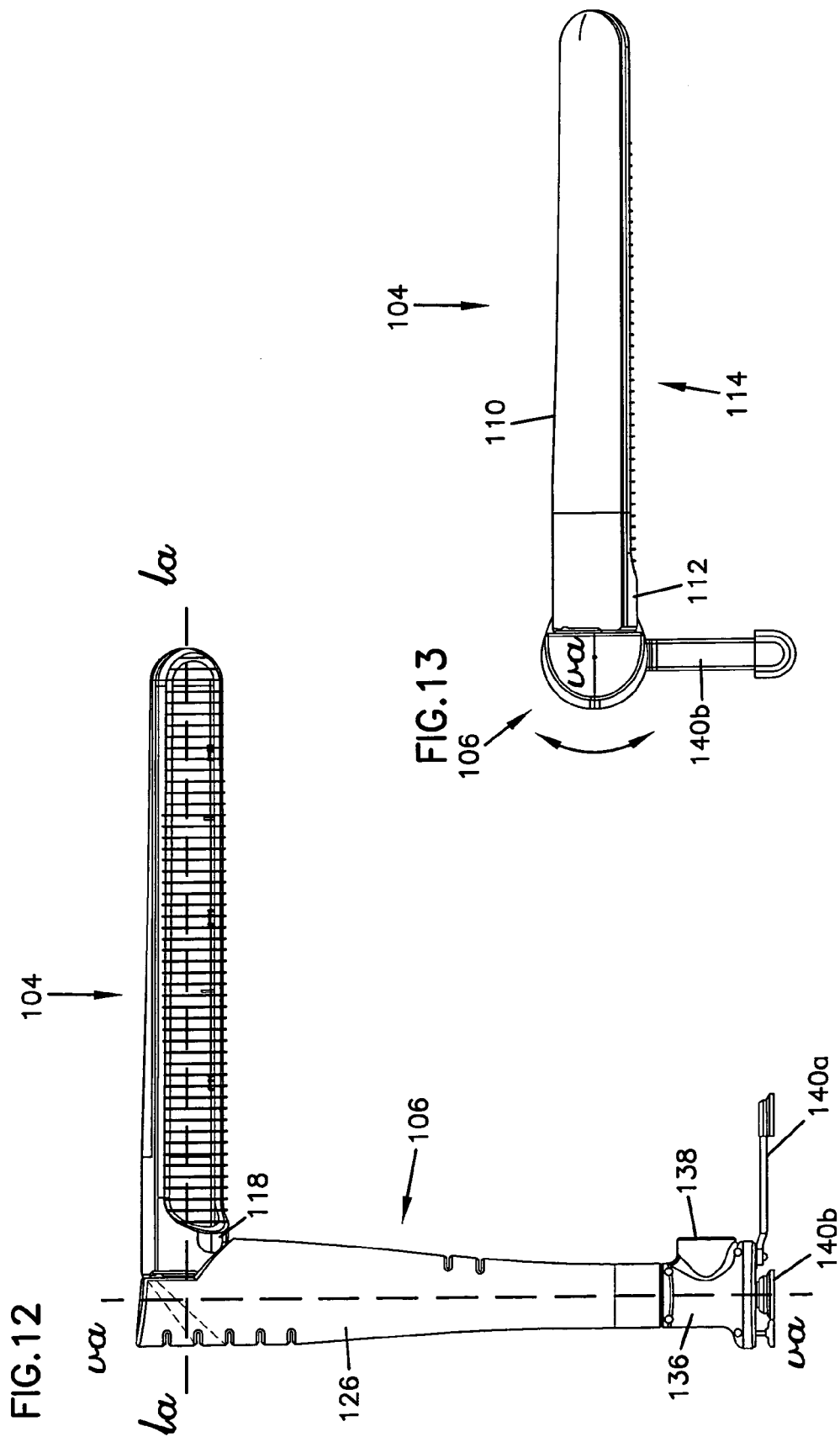

FILTERED AIR

UNFILTERED AIR

AIR EXIT

AIR ENTRANCE

FIG.22A
FIG.22B
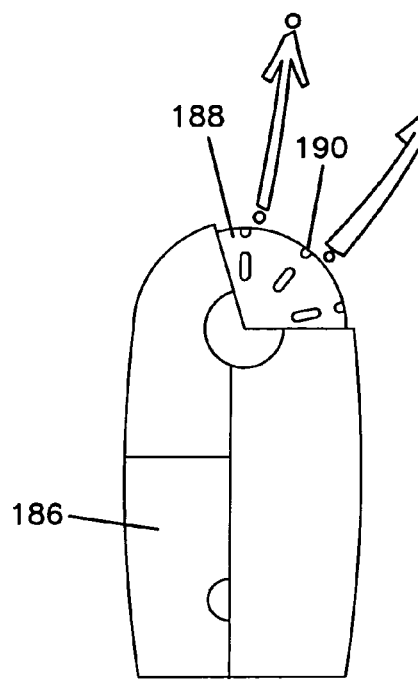
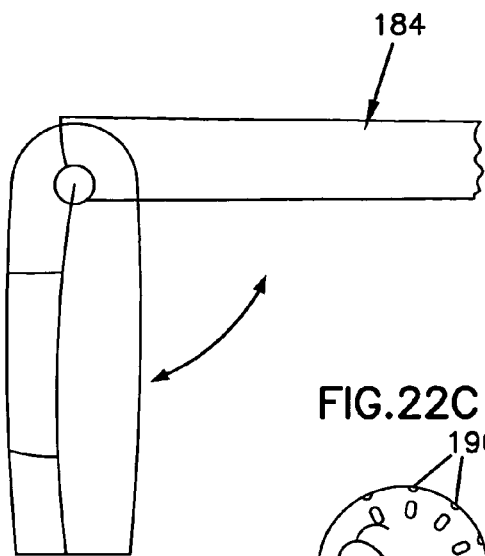
FIG.22C
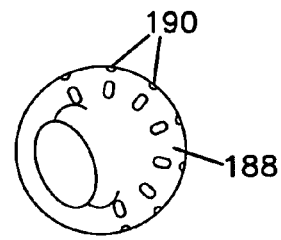
FIG.23A
FIG.23B
FIG.23C
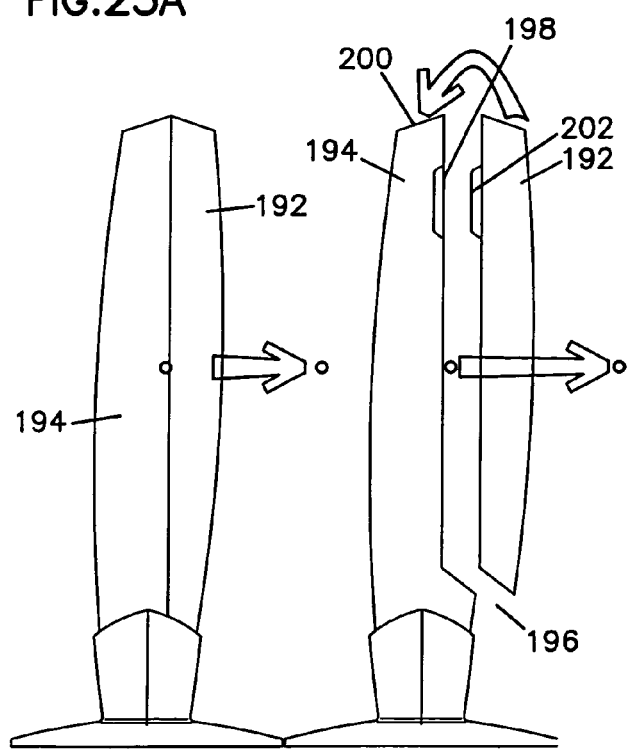
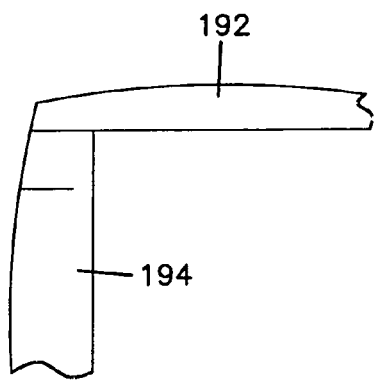

SYSTEMS FOR DELIVERING CONDITIONED AIR TO PERSONAL BREATHING ZONES

This application claims the benefit Provisional Application Ser. No. 60/461,306 filed on Apr. 8, 2003, and claims the benefit of Provisional Application Ser. No. 60/539,360 filed on Jan. 27, 2004.

FIELD OF THE INVENTION

This invention relates to systems for delivering conditioned air to personal breathing zones. More particularly, this invention relates to systems in the personal environment that deliver conditioned air to improve health or comfort.

BACKGROUND OF THE INVENTION

Asthma in the U.S. and around the world has increased at an alarming rate over the last 20 years and currently affects more than 15 million Americans. There is some speculation as to the cause of this increase, whether due to more time spent indoors in "tighter" homes with less fresh air or because of improvements in early diagnosis of disease. A recent study concluded that the risk due to residential allergen and pollutant exposure accounted for 39% of doctor-diagnosed asthma in U.S. children less than 6 years old. 5,000,000 U.S. children (1 in 13) now suffer from asthma, accounting for 17% of all pediatric emergency room visits.

Allergic rhinitis or hay fever affects 40 million Americans. It can lead to rhinosinusitis (in 14% of the U.S. population) as well as otitis media (e.g. ear ache), the most common childhood disease requiring a healthcare visit.

In addition to the tremendous discomfort associated with these diseases and their all too often tragic outcomes (there are more than 5,000 asthma related deaths per year in the U.S.), the estimated annual cost of asthma in the U.S. is projected to be $14.5 billion this year, up from $6.2 billion only 10 years ago.

The first line of defense against these disease's symptoms recommended by allergists is to reduce environmental exposure. This can be accomplished by removing the allergen source (for example cats, cigarettes, molds, etc.), its reservoir (for example carpets, drapes, etc.) and also by cleaning the air through the use of high-efficiency air cleaners.

Existing air cleaner technology can be very effective at removing a high percentage of particles in the air stream passing through them by means of High Efficiency Particulate Air (HEPA) filters, electrostatic precipitators, etc.

The efficacy of these filters on the particle levels people actually breath, however, is directly dependent on the filter's efficiency, air changes per hour or airflow, and dynamics of the environment such as open doors or windows, forced air ventilation and particle sources within the room. Studies show that these variables, through mixing with the filtered air, can decrease a HEPA (typically 99.97% efficient) filters' effect on room particle counts to an average efficiency of 50% or less where the rooms' occupants are breathing.

As an example, people often utilize room air cleaner units in an attempt to achieve a reduction in particles levels within a localized area. These types of units effectively remove a high percentage of harmful particles from the air that flows through the unit. However, individuals within the area of the unit may not experience all of the beneficial results of this particle removal because the air that is discharged from the unit is able to pick up additional harmful particles from the surrounding environment prior to reaching and being breathed in by the individuals.

SUMMARY OF THE INVENTION

The invention provides a system to significantly improve the air quality in a personal breathing environment. Air quality can be improved by one or more of the following: removing allergens and other harmful particles from an air stream prior to the air stream reaching the personal breathing environment; preventing allergens and other harmful particles from reaching the personal breathing environment; and conditioning the air in the personal breathing environment.

The invention comprises a blower unit, a delivery system that delivers air provided by the blower unit to a person's breathing zone, and a conduit that interconnects the blower unit and the delivery system for directing air from the blower unit to the delivery system. The delivery system is positioned so that it sends conditioned air around a persons head and into their personal breathing zone. The air delivered by the delivery system creates a zone of conditioned air around the persons head. Allergens and other harmful particles are prevented from entering the zone of conditioned air, so that the air being breathed in by the person is substantially the conditioned air delivered by the delivery system.

In one aspect of the invention, the delivery system is positioned relative to a bed for delivering conditioned air around the head of a person or persons laying on the bed. The delivery system can also be positioned relative to a person sitting or laying on a chair, sofa or other piece of furniture for delivering conditioned air around that persons head, or positioned within a vehicle for delivering conditioned air around the head of an occupant of the vehicle. Many variations are possible. Indeed, the delivery system can be used in any location where it would be desirable to deliver conditioned air around a persons head while that person is sitting, standing or laying down.

The blower unit is preferably provided with a high efficiency filter which filters the air prior to being delivered to the breathing zone. The air can also be conditioned in other manners, for example heating or cooling the air, humidifying the air, introducing aromas and medicines into the air, and the like.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying description, in which there is described a preferred embodiment of the invention.

BRIEF DESCRIPTION OF THE DRAWINGS

FIG. 1 is a schematic representation of the system of the invention, depicting a blower unit delivering air to a delivery system.

FIG. 2 illustrates an embodiment of the invention arranged relative to a bed.

FIG. 12 is a view of the embodiment of FIG. 11 in an assembled condition.

FIG. 13 is a top view of the embodiment of FIG. 11.

FIGS. 22A–C illustrate another embodiment of the invention that utilizes a pivoting air delivery system.

FIGS. 23A–C illustrate another embodiment of the invention that utilizes another embodiment of an air delivery system.

DETAILED DESCRIPTION OF THE PREFERRED EMBODIMENT(S)

The present invention, as schematically depicted in FIG. 1, provides a system 10 for delivering conditioned air around one or more person's head, i.e. in their personal breathing zone. The system 10 includes a blower unit 12, a delivery system 14, and a conduit 16 that interconnects the blower unit 12 and the delivery system 14 for directing air from the blower unit to the delivery system.

The blower unit 12 is preferably provided with a high efficiency filter which filters the air prior to being delivered to the breathing zone. The air can also be conditioned in other manners, for example by one or more of heating or cooling the air, humidifying the air, introducing aromas and medicines into the air, and other conditioning. The delivery system 14 is preferably arranged near a persons head so that it delivers the conditioned air around the person's head and into their personal breathing zone, thereby improving the quality of the air that is breathed by the person. In addition, the conditioned air that is delivered helps to keep ambient air, which can contain a high level of allergens, from being breathed in by the person by creating a zone of conditioned air around the person's head.

The preferred embodiment(s) will be described herein with respect to delivering conditioned air to the personal breathing zone of a person laying on a bed. It is to be realized that the system 10 could be utilized in other environments as well, for example delivering conditioned air to a person sitting or laying on a chair or sofa, or while a person is situated in a motor vehicle.

Figure 3:
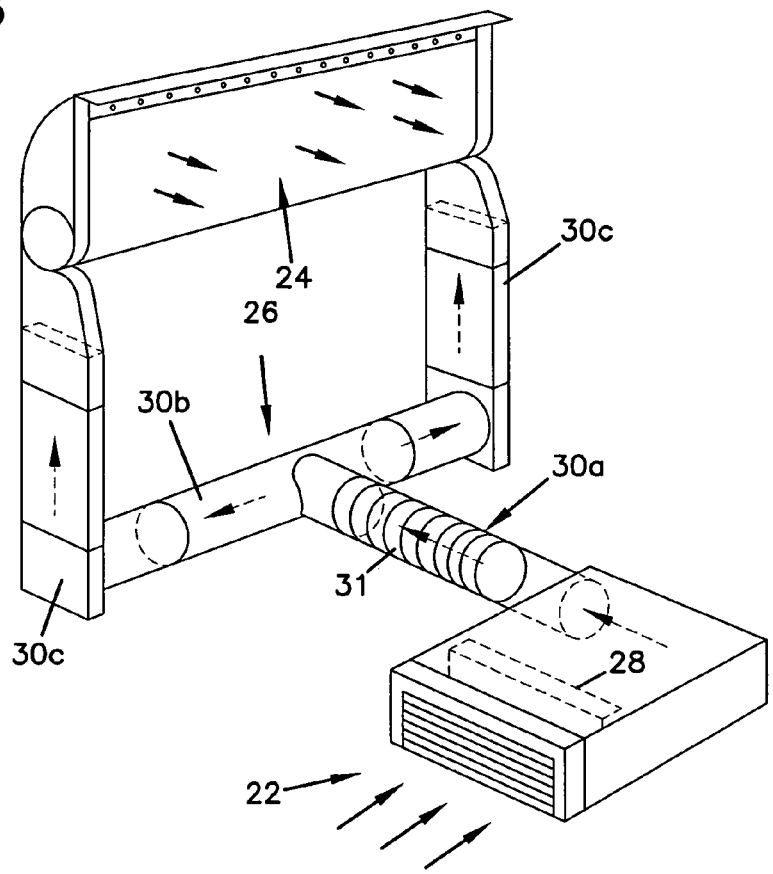
FIG. 3 illustrates the system of FIG. 2 with the bed removed for clarity.

With reference now to FIGS. 2 and 3, a system 20 that is similar to the system 10 is shown relative to a bed 21. The bed 21 is illustrated as being able to accommodate two sleeping adult individuals. However, it is to be realized that the bed 21 can be any size bed, including single, double, twin, queen or king sized, accommodating adults or children.

The system 20 includes a blower unit 22, a delivery system 24 and a conduit 26 connecting the blower unit 22 to the delivery system 24. The blower unit 22 preferably includes a blower wheel (not shown) driven by an electric motor (not shown) for creating a flow of air. A high efficiency filter 28, such as a HEPA filter, is disposed in the blower unit 22 for filtering the air. The filter 28 is preferably at least about 80% efficient at removing respirable particles at least 0.3 microns and greater in size, more preferably the filter is at least about 90% efficient at removing respirable particles at least 0.3 microns and greater in size, and most preferably the filter 28 is at least about 95% efficient at removing respirable particles at least 0.3 microns and greater in size.

Many conventional air filtration mechanisms, such as room air cleaners, are advertised as having a high efficiency, such as 95%. It is to be realized that the efficiency that is achieved in such conventional mechanisms is measured relative to the air immediately after the air exits the filter. Therefore, although the air at the moment in time it leaves the filter is highly filtered, the filtered air picks up allergens and other contaminants as it mingles with room air prior to being breathed in. As a result, in a room with such a mechanism, the air that is ultimately breathed in is typically well below the advertised filtration efficiency of the mechanism. In contrast, with the system described herein, the air that is ultimately breathed in by the person has substantially the same filtration efficiency as the air exiting the filter 28. Therefore, if the air is 95% free of respirable particles at least 0.3 microns and greater in size (i.e. the filter is 95% efficient) as it exits the filter 28, the air that is breathed in by the person within the zone of conditioned air is 95% free of respirable particles at least 0.3 microns and greater in size.

The conduit 26 includes a duct 30a that connects to the blower unit 22 and receives the airflow therefrom. A second duct 30b is connected to the duct 30a for delivering air to opposite sides of the bed 21. Each end of the duct 30b is connected to a riser duct 30c, each of which extends upwardly from adjacent the end of the bed from the floor up to the delivery system 24 to deliver air to the delivery system 24. The blower unit 22, the duct 30a and the duct 30b are sized to enable them to fit underneath the bed 21 resting on the floor, thereby minimizing their visibility.

Figure 5:
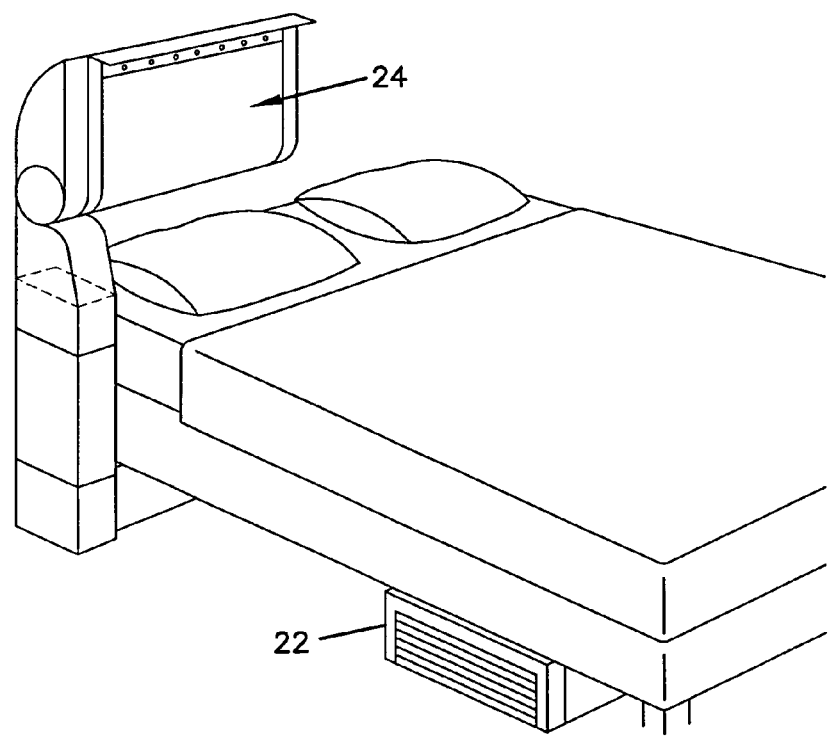
FIG. 5 illustrates yet another embodiment of the invention.

In the illustrated embodiment, the delivery system 24 extends the width of the bed 21 between the riser ducts 30c, and is located at the end of the bed where a headboard may often be located. In this embodiment, the delivery system is positioned to blow air across the tops of the pillows so that conditioned air would be delivered around the heads and into the personal breathing zones of each person laying on the bed. However, as illustrated in FIG. 5, the delivery system 24 could extend along only a portion of the width of the bed, in which case conditioned air would be delivered around the head of only one person. In the embodiment in FIG. 5, the second riser duct 30a would not be necessary.

Portions of the air delivery conduit 26, for example riser ducts 30c, have been illustrated as being disposed to the sides of the bed. However, it is contemplated that air could be delivered from below the bed to above the bed through ducting that is disposed at the end of the bed between the headboard (if used) and mattress and the wall of the room in which the bed is located.

The delivery system 24 comprises a generally hollow structure defined by a front panel 32 that is designed to permit air to flow therethrough, and an air impermeable rear panel 34. The delivery system 24 is connected to the riser ducts 30c in such a manner as to permit conditioned air to flow from the riser ducts into the interior of the system 24.

The front panel 32 is made of, for example, air permeable or perforated fabric. Alternatively, the front panel 32 can be made of a hard plastic material that is provided with perforations or holes to permit air flow through the front panel 32. The rear panel 34 can be formed of any suitable air impermeable material, such as fabric or a hard plastic.

The use of a fabric rear panel 34 together with a fabric front panel 32 will define a system 24 that can collapse upon itself when airflow is not being provided by the blower unit 22, and which will reexpand when airflow is provided. The use of a plastic rear panel 34 together with a plastic front panel will define a system 24 that maintains its shape when airflow is not provided.

The system 24 is positioned so that conditioned air that flows into the system 24 and out through the front panel 32 is directed around the heads of the individuals laying on the bed and into their breathing zone. As a result, the individuals breath in conditioned air that is substantially free of allergens.

The system 24 is also provided with a deflector 36 along the top edge thereof for deflecting air downward and out toward the individuals on the bed. In addition to, or alternatively of, the deflector 36, the front panel 32 can be provided with vent holes 38 adjacent the top edge thereof. The vent holes 38 create an air dam or air deflector above the air delivery area. A significant advantage of the deflector 36 and/or the air dam created by the vent holes 38 is that the influence of competing air streams and currents that are present in the room, which can adversely effect the clean air envelope that is developed around the person's head, are reduced.

The delivery system 24 can be designed to be maintained in the position shown in FIG. 2. Alternatively, the system 24 can be designed to pivot downward (as shown by the arrow in FIG. 2) to a non-use position where the front panel 32 is disposed substantially above the pillows on the bed. Moreover, the system 24 can take the place of a headboard that is often found on bed frames, as shown in FIG. 2. If the bedframe includes a headboard, the system 24 can be disposed in front of the headboard. In addition, the system 24 and the headboard could be integrated together, whereby the system 24 is built into, and is an integral component of, the headboard.

Further, the riser ducts 30c can be adjustable vertically to enable adjustment of the vertical height of the system 24. In addition, controls for controlling operation of the blower unit 22 can be incorporated into the riser ducts 30c or into the system 24. Alternatively, a handheld remote control unit can be provided, with the remote control unit operating via suitable known wireless technology to control blower unit operation.

Figure 4:
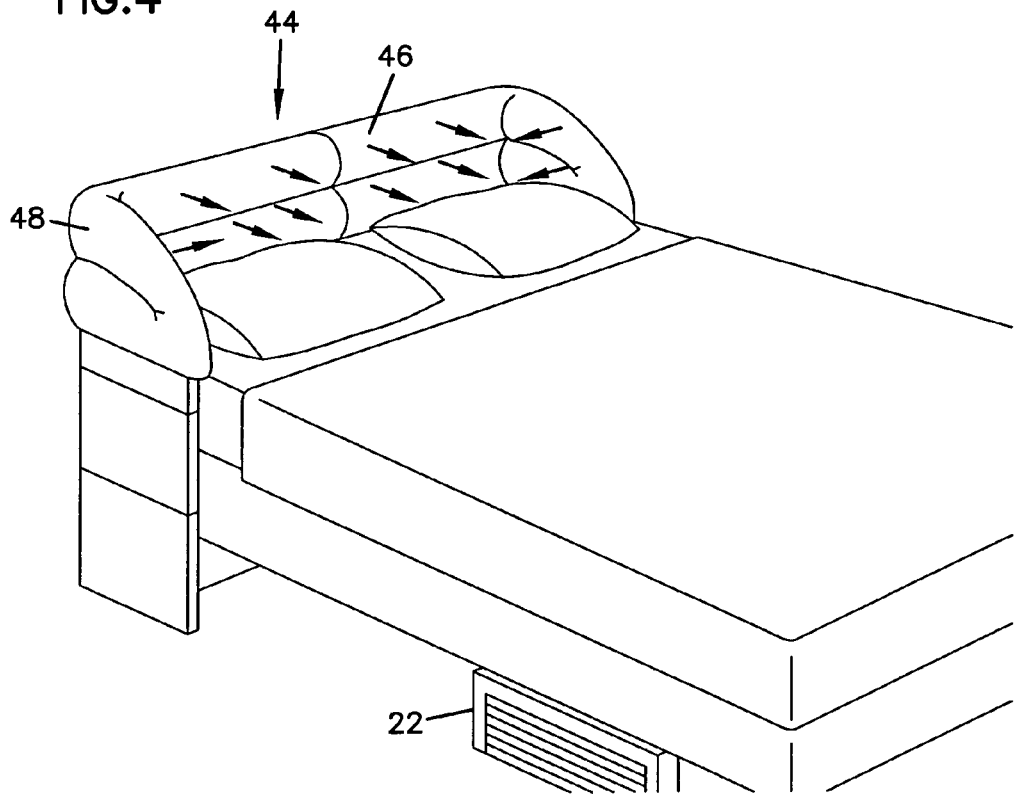
FIG. 4 illustrates another embodiment of the invention.

Numerous configurations of the delivery system are possible. FIG. 4 illustrates a delivery system 44 in the form of a "U"-shaped collar that includes side sections at the ends of a rear section. The system 44 comprises an air permeable front portion 46 (i.e. those portions that face or are toward the individuals), preferably made of air permeable fabric, and an air impermeable rear portion 48 (i.e. those portions that face away from the individuals), preferably made of air impermeable fabric. As with the embodiment in FIG. 5, the system 44 need not extend the entire width of the bed. Further, the system 44 could utilize a front portion 46 that comprises perforated plastic or perforated fabric.

Figure 6:
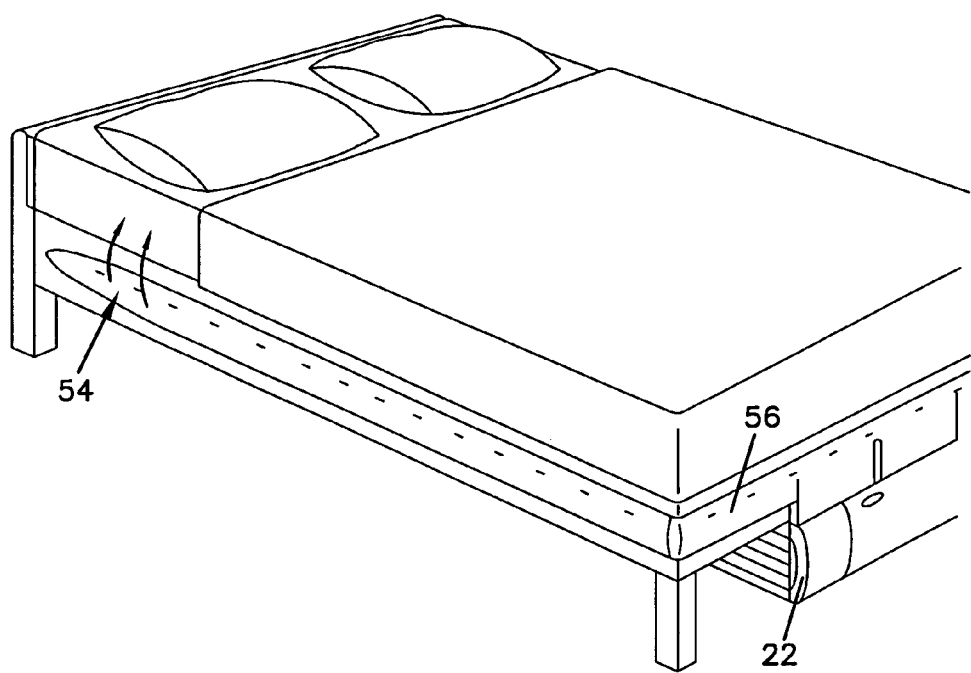
FIG. 6 illustrates yet another embodiment of the invention.

FIG. 6 illustrates a delivery system 54 that is connected to or integrated into the sides of the bedframe or the mattress. Conditioned air is introduced into a conduit 56 which is connected to or integrated into the bedframe or mattress at the foot end thereof, which directs the conditioned air to the system 54.

Figure 7:
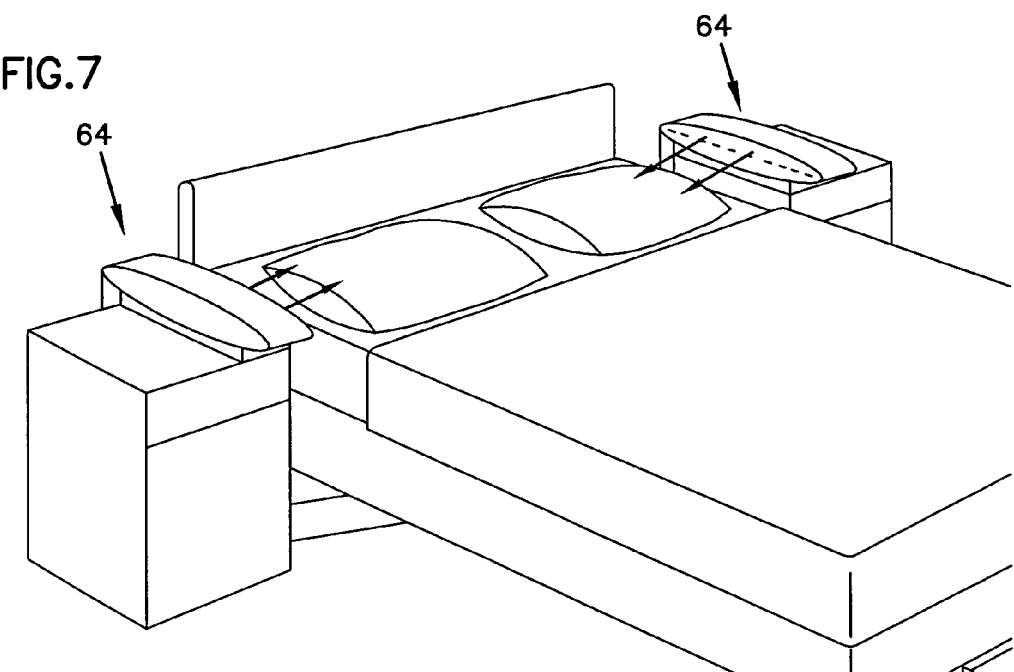
FIG. 7 illustrates yet another embodiment of the invention.

FIG. 7 illustrates a delivery system 64 that is not directly connected to or supported by the bed. Instead, the delivery system 64 is supported adjacent to the bed for directing conditioned air around the individual's heads.

Figure 8:
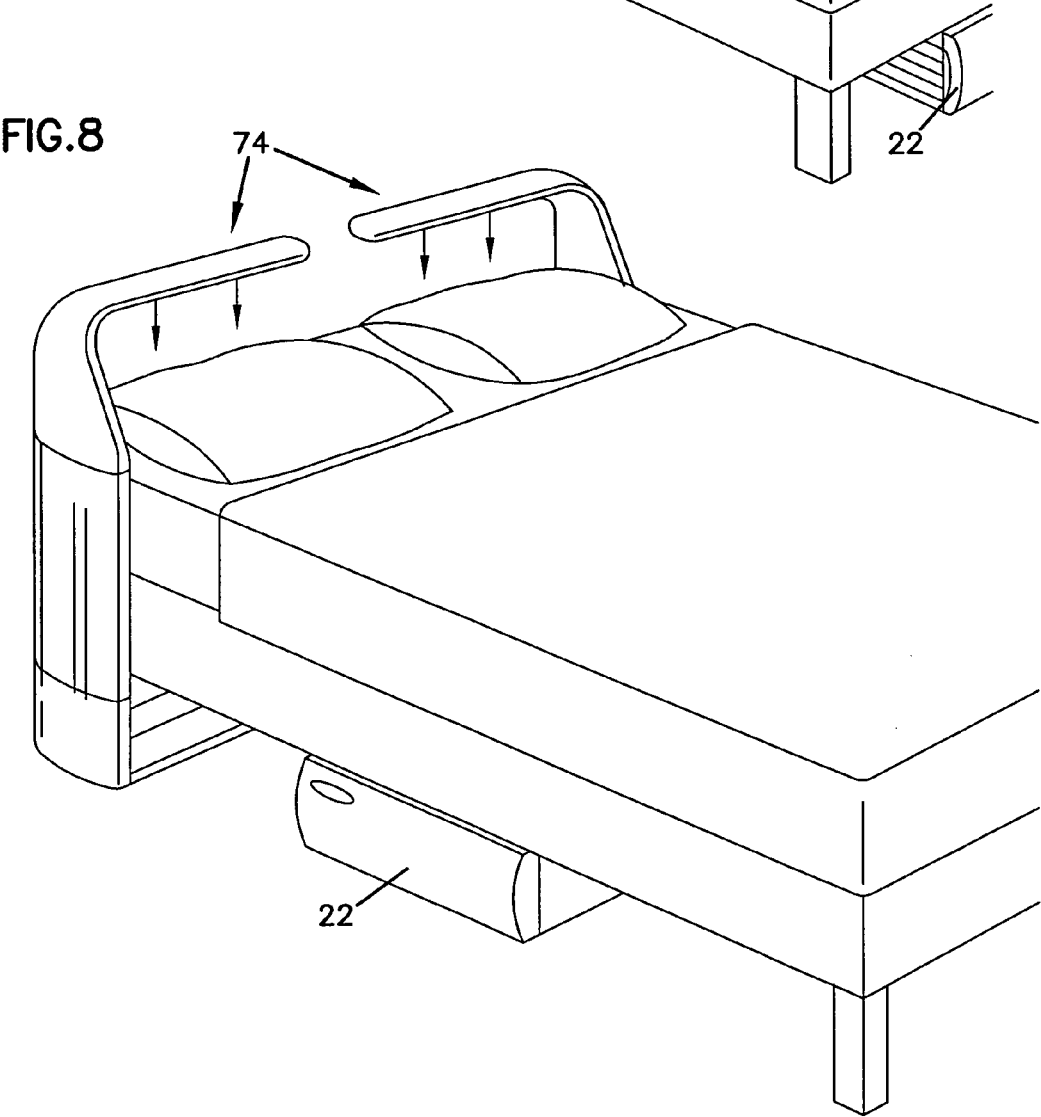
FIG. 8 illustrates yet another embodiment of the invention.

FIG. 8 illustrates a delivery system 74 that comprises delivery wands that extend over the pillows on the bed. The system 74 is configured so that it delivers conditioned air downward toward the individuals.

Figure 9:
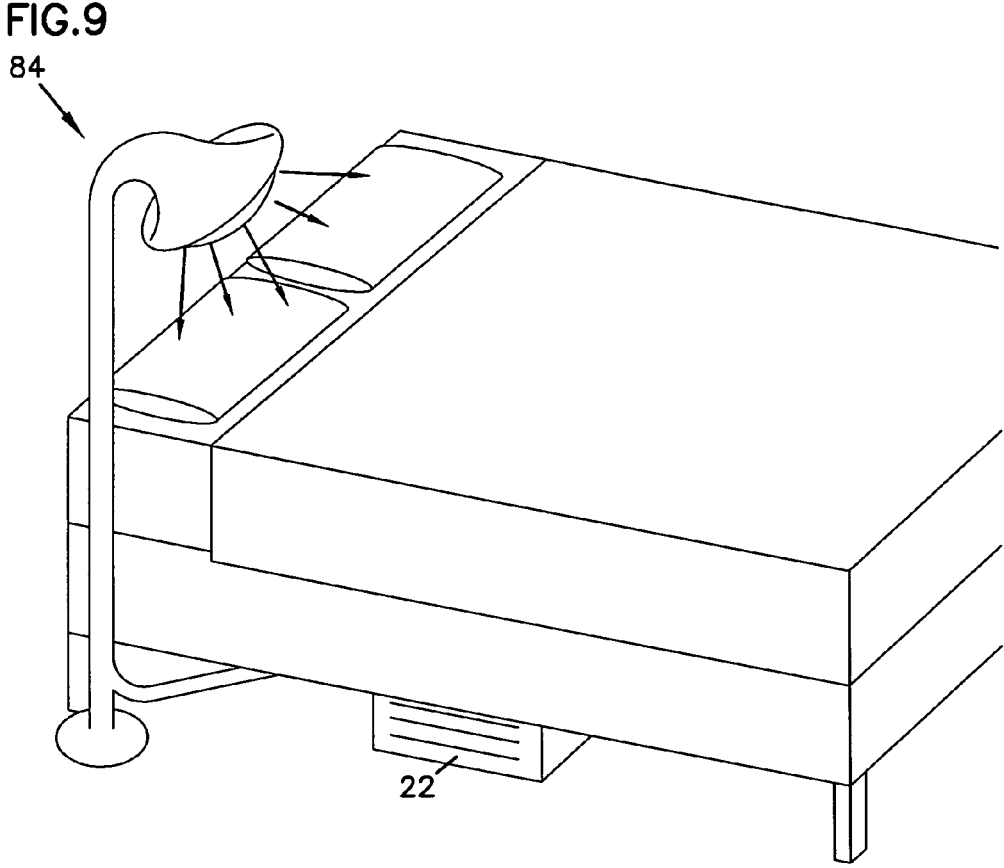
FIG. 9 illustrates yet another embodiment of the invention.

FIG. 9 illustrates a delivery system 84 in the form of a shower head like device that extends over the pillows on the bed. The system 84 delivers conditioned air downward toward each pillow.

Figure 10:
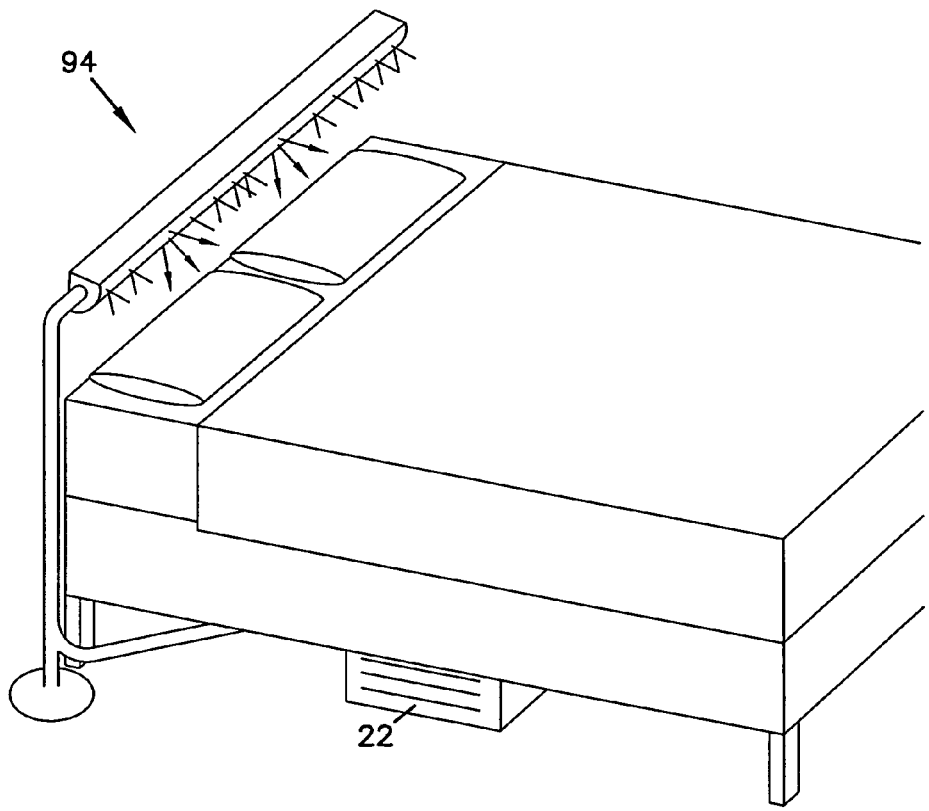
FIG. 10 illustrates yet another embodiment of the invention.

FIG. 10 illustrates a delivery system 94 that comprises a quarter round arrangement where the flat sides of the system 94 are substantially air impermeable, while the arcuate side of the system 94 is air permeable to direct air both downwardly toward and above the pillows.

Another embodiment of the invention will now be discussed with reference to FIGS. 11, 11a, 12–18. In this embodiment, the air delivery system is in the form of a cantilever supported boom 104 that is attached to and extends from a tower 106 that forms a portion of the conduit connecting the boom 104 to a blower unit 108 (shown in FIGS. 18–20).

Figure 11:
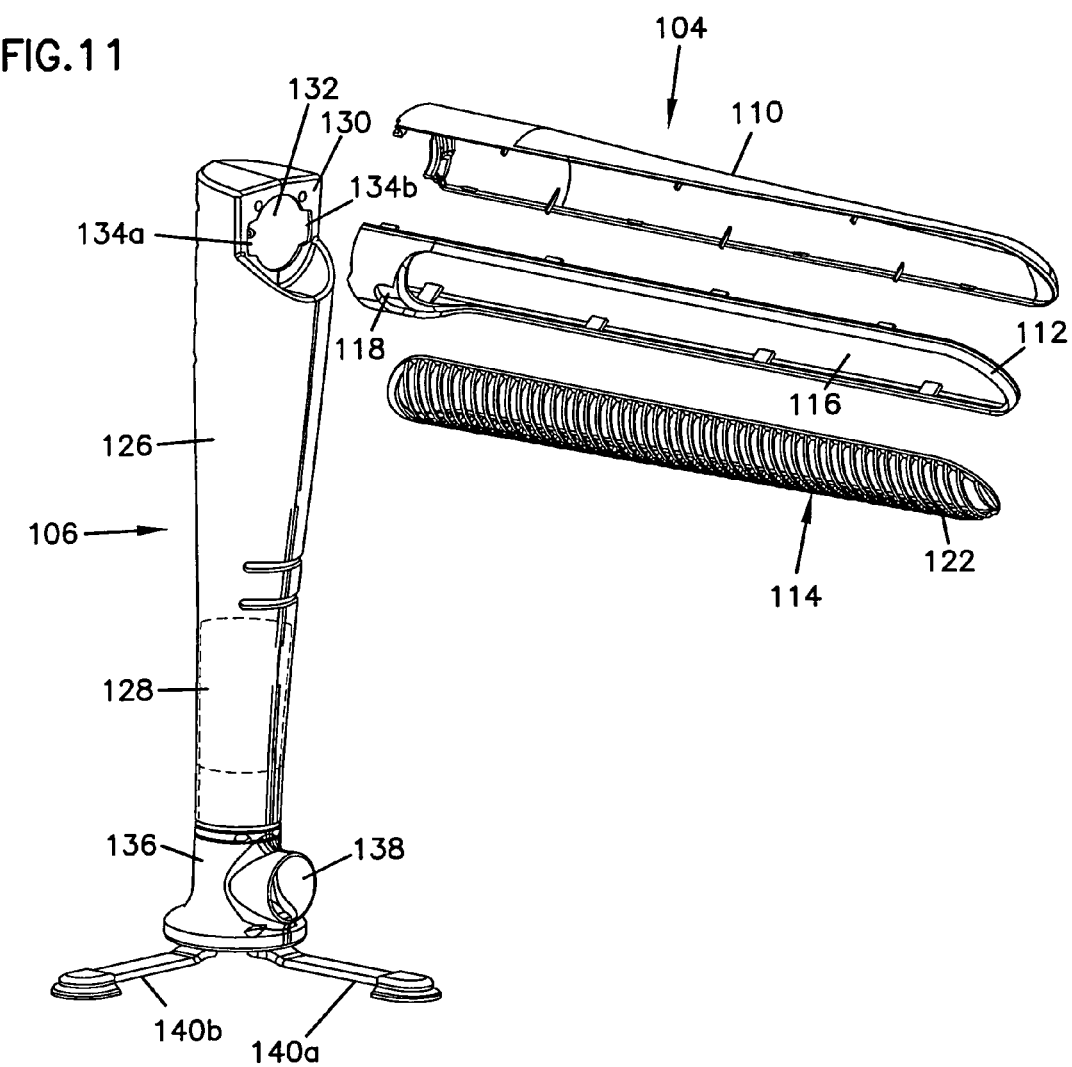
FIG. 11 is an exploded view of another embodiment of the invention.

As illustrated in FIG. 11, the boom 104 is a multi-piece construction comprising a rear housing section 110, a forward housing section 112, and an air outlet section 114. The housing sections 110, 112 connect together to define a generally hollow structure defining a passage for the flow of air. The boom 104 decreases or tapers in size from the end that connects to the tower 106 to its free, unattached end, whereby the airflow passage also decreases in size. The airflow passage in the boom 104 distributes the air along the length of the boom, with the tapered shape of the airflow passage configured to maintain the pressure of the air along the length of the boom 104 so that a generally constant air discharge pressure, a generally constant air discharge velocity, and a generally constant air discharge volume from the boom are achieved from the air outlet section 114 along the length of the boom 104. The boom could also have a constant size from its connected end to its free end, while the airflow passage with the boom is appropriately configured to taper in size as discussed above.

The front housing section 112 includes an opening 116 that extends the majority of the length thereof, and the air outlet section 114 detachably fits into the opening 116. The opening 116 has a generally constant size from one end thereof to the other end, so that air in the airflow passage of the boom 104 can exit the boom through the opening 116 and the outlet section 114 covering the opening 116. The detachable connection of the outlet section 114 into the opening can be achieved through a snap fit connection, via a friction fit, using screws, or using other forms of detachable connection means. As shown in FIGS. 11, 11A, 12 and 13, the housing section 112 includes a recessed portion 118 that allows the user to get his finger(s) under the end of the outlet section 114 to initiate removal of the outlet section.

Figure 11A:
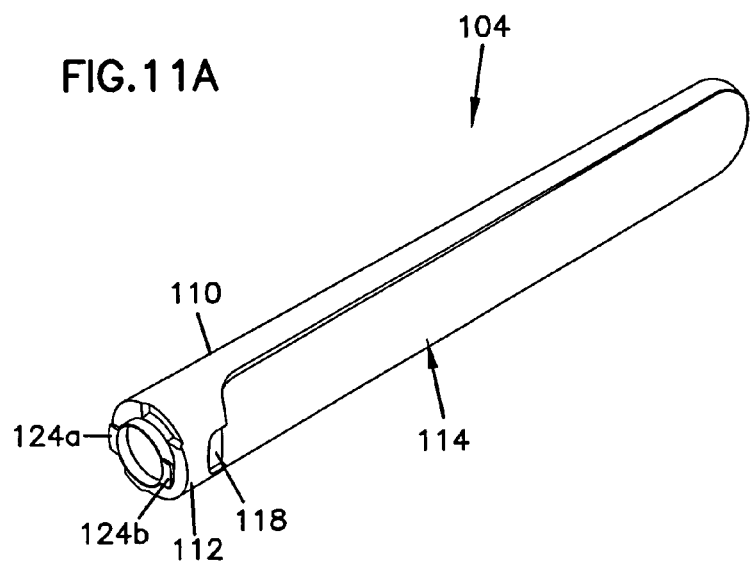
FIG. 11A illustrates the boom of FIG. 11 with the fabric cover in place on the frame.

The housing sections 110, 112 can be made of a material, for example plastic, that is generally impermeable to air so that substantially all of the air that enters the boom 104 exits through the opening 116 and the outlet section 114. The outlet section 114 is formed by an air permeable fabric material cover 120 supported on a frame 122. FIG. 11A illustrates the cover 120 in place on the frame 122, while FIGS. 11, 12 and 13 illustrate the frame 122 without the cover 120.

In the illustrated embodiment, the frame 122 is a grill-like structure formed of plastic. The cover 120, which in use is supported by the frame 122, is preferably removably supported on the frame 122 to permit its removal for washing or replacement. In one implementation, the cover 120 can be a sleeve that is slid over the frame 122. In another implementation, the cover 120 is a panel that attaches to the exterior of the frame 122. Regardless of how the cover 120 is configured, the cover 120 preferably covers at least the exterior of the frame 122 to improve the aesthetic appearance of the boom 104.

Figure 14A:
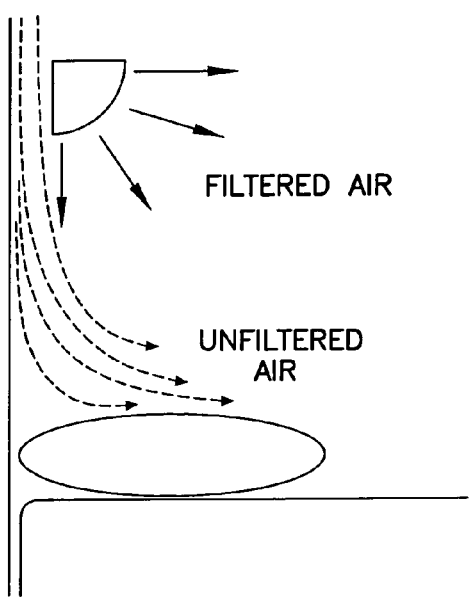
FIGS. 14A and 14B illustrate the effect of an air dam created by the air delivery system of FIGS. 11–13.
Figure 14B:
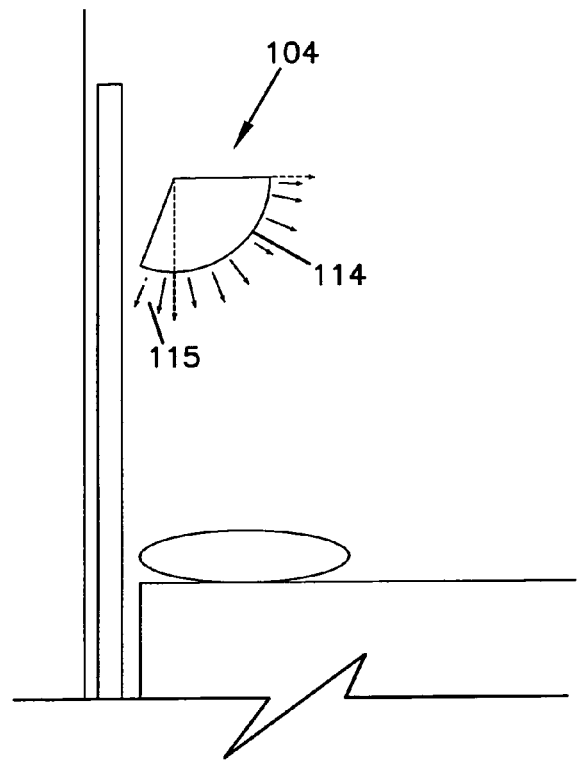

As shown in FIG. 14B, the outlet section 114 has a generally curved cross-sectional shape. The cross-sectional shape of the outlet section 114 could have numerous configurations, including a single curved surface, a plurality of curved surfaces having differing curvatures, a series of interconnected straight segments, or a combination of straight and curved sections.

Whichever configuration is used, it is preferred that the outlet section 114 be configured to discharge air over an arc that is sufficient to create an air dam that improves the resulting zone of conditioned air that is created. With reference to FIG. 14A, for an outlet section that discharges air over an arc of 90 degrees, air from the top of the outlet section exits generally parallel to the bed surface, while air from the bottom of the outlet section exits generally perpendicular to the bed surface. With such a configuration, the air from the bottom of the outlet section tends to entrain unfiltered air and pull the unfiltered air downward from behind the boom 104 toward the bed surface. This results in an increase in the amount of contaminated air that enters the zone of conditioned air, thereby decreasing the quality of the air that is within the zone.

In contrast, the boom 104 is configured so that a portion 115 of the filtered air is discharged from the outlet section 114 toward the bedframe or wall disposed behind the boom. This discharged air 115 creates an air dam that prevents unfiltered air from being pulled downward behind the boom 104 and into the conditioned air zone. It has been found that discharging air over an arc of at least approximately 110 degrees, as is illustrated in FIG. 14B, provides satisfactory results. Preferably, the air is discharged over an arc length of from about 7.0 inch to about 8.0 inch, and an arc angle of from about 120 degrees to about 130 degrees, with about 30 degrees to about 40 degrees of arc back of vertical (shown in dashed lines), as shown in FIG. 14B. However, it is to be realized that the air could be discharged over other arcs as well, as long as the air dam effect is created.

Figure 15:
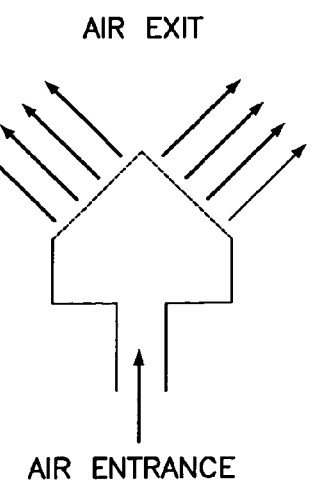
FIG. 15 illustrates how the air leaves through the fabric of the air delivery system.

Moreover, it has been discovered that the air leaving the cover 120 of the outlet section 114 tends to have a primary velocity vector that is generally perpendicular to the surface from which it exits at the range air flow rates that are later described herein, as illustrated in FIG. 15. Moreover, the fabric that is used for the cover 120 is preferably one where the relationship between the pressure drop across the fabric face and the velocity of the air leaving the fabric face is defined as:

$$\Delta P = 0.001415 * V^{1.149}$$

where $\Delta P$ is the pressure drop in inches of water, and V is the velocity of air leaving the face of the fabric cover in feet per minute.

Therefore, for an air velocity of 40 ft/min leaving the fabric face, the pressure drop across the fabric face of the cover 120 is preferably approximately 0.100 inches of water.

Returning now to the boom in FIGS. 11, 11A, 12 and 13, the supported end of the boom 104 includes a pair of flanges 124a, 124b that are used to detachably secure the boom 104 to the tower 106, as will be explained in further detail below. The flanges 124a, 124b are visible in FIG. 11A, as well as FIG. 16 which illustrates a boom that is similar to the boom 104 illustrated in FIGS. 11, 11A, 12 and 13, but where the air discharge opening in the boom tapers in size such that the size of the opening decreases from one end thereof to the other end. The boom in FIG. 16 and the boom 104 in FIGS. 11–13 attach to the tower 106 in identical fashion.

Figure 17:
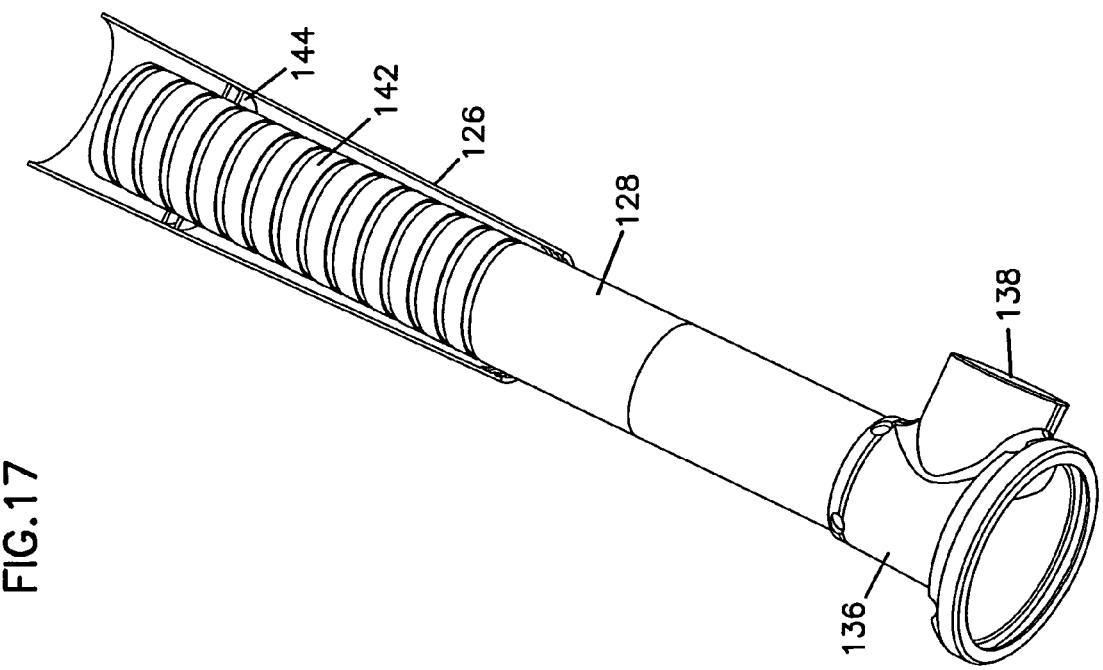
FIG. 17 illustrates a portion of the air delivery conduit, with portions broken away to show the vertical height adjustment feature.

The tower 106 is also a multi-piece construction comprising an upper tower section 126 and a lower tower section 128, as shown in FIGS. 11 and 17. The tower sections 126, 128, which are preferably formed of a plastic material, are generally cylindrical, with the tower section 126 configured to fit over the tower section 128 in a telescoping arrangement with a relatively close fit between the two sections, as illustrated in FIG. 17. The tower section 128 disposed inside of the tower section 126 has a generally constant diameter from bottom to top, while the tower section 126 has a lower portion of generally constant diameter that transitions into an upper portion that increases in diameter. Thus, the conduit formed by the tower sections 126, 128 increases in diameter as the conduit nears the top of the tower section 126. The increasing diameter serves to slow and smooth the airflow through the tower 106 prior to the airflow entering the boom 104, thereby reducing noise resulting from turbulence. The illustrated shape of the tower sections 126, 128 also enhances the aesthetics of the tower 106.

The tower section 126 includes a notched section 130 at the top thereof where the boom 104 attached to the tower 106. The notched section 130 includes a hole 132 with cut-outs 134a, 134b that receive the end of the boom 104. It has been found that a diameter of the hole 132 (ignoring the cut-outs 134a, 134b) of about 3.5 inches works well in serving to minimize the air velocity as it enters the boom. To connect the end of the boom 104 to the tower 106, the end of the boom 104 is aligned with the hole 132, with the flanges 124a, 124b aligned with the cut-outs 134a, 134b respectively. The end of the boom 104 is then pushed into the hole, and rotated 45 to 90 degrees thereby displacing the flanges 124a, 124b relative to the cut-outs 134a, 134b and locking the boom 104 to the tower 106. Air flowing upwardly through the tower 106 is able to flow through the end of the boom 104 for distribution along the length of the boom. To smooth the transition of the air into the end of the boom, a deflection plate (shown in dashed lines in FIG. 12) disposed at around 45 degrees to the vertical axis of the tower 106, or a curved deflection plate (shown in dashed lines in FIG. 12) can be provided in the upper end of the tower section 126 to transition air into the boom 104.

The lower tower section 128 is connected to a base section 136 that includes an inlet 138 to which a hose (not shown) leading from the blower unit 108 connects. It has been found that a diameter of the inlet 138 of at least about 3.0 inches works well. The base section 136 preferably has a substantial weight to lower the center of gravity of the unit, thereby increasing the stability of the unit. To provide adequate weight, the base section 136 can be formed of a relatively heavy material such as metal. Alternatively, the base section 136 could be formed of plastic, and have weights attached thereto to increase its overall weight. Similar to the upper tower section 126, the lower tower section 128 can include a deflection plate disposed at around 45 degrees to the vertical axis of the tower 106, or a curved deflection plate can be provided in the lower end of the tower section 128, to transition air into the tower from the inlet 138.

A pair of support legs 140a, 140b are connected to the base of the base section 136 for supporting the unit on the floor. The legs 140a, 140b are adjustably mounted so their position relative to the base section 136, and relative to each other, can be altered. Adjustability of the support legs 140a, 140b is important because the system must be able to interact with the feet of numerous beds and headboards, as well as with the feet of nightstands and other furniture adjacent beds. Therefore, by making the support legs adjustable, the legs can be positioned to avoid such obstacles.

As described above, the boom 104 is attached to the tower 106 in such a manner as to permit adjustment of the boom 104 about its own longitudinal axis la. Thus, the direction of the air flow from the boom 104, and the resulting zone created around the person on the bed, can be altered by rotating the boom 104 slightly one way or the other around its own axis.

The unit is also preferably designed so that the boom 104 can rotate about the vertical axis va of the tower as shown by the arrow in FIG. 13, to enable the unit to be used on either the left or right side of the bed. To accomplish this, the tower section 126 is preferably rotatable relative to the lower tower section 128 about the vertical axis so that the boom 104 can be positioned on the opposite side of the tower 106 from the position shown in FIG. 12. The boom 104 would also need to be repositioned so that the air is discharged in the proper direction.

The tower 106 is also height adjustable so that the height of the tower 106, and the resulting height of the boom 104 above the bed, can be adjusted according to the user's needs. Height adjustment can be accomplished in many ways. One way to achieve height adjustment is shown in FIG. 17. In this version, the exterior of the upper portion of the tower section 128 is provided with a threaded section 142 having a spiral groove. The interior surface of the tower section 126 is provided with threads 144 that engage with the groove of the threaded section 142. As the tower section 126 is rotated relative to the tower section 128, the engagement between the threads 144 and groove cause the tower section 126 to raise or lower relative to the tower section 128, depending upon its direction of rotation. Such rotation can be caused manually by the user. Thus, the threaded height adjustment shown in FIG. 17 is capable of achieving infinite height adjustment within the height adjustment range permitted by the threaded section 142 and the threads 144.

Figure 18:
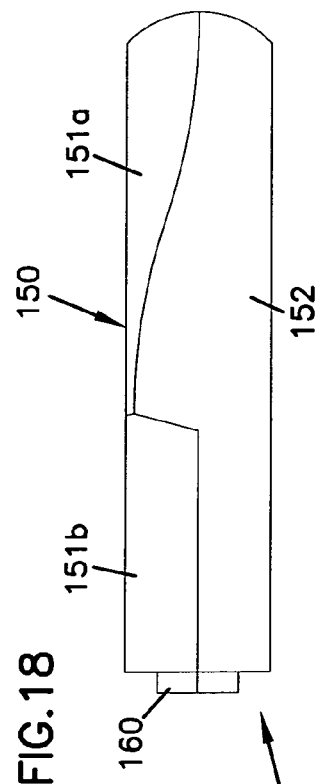
FIG. 18 is a side view of an embodiment of the blower unit.
Figure 20:
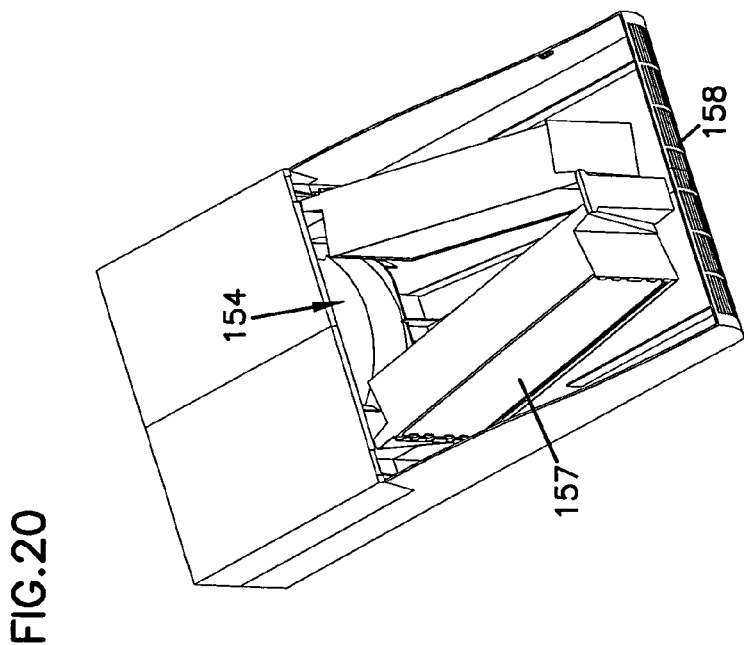
FIG. 20 is a perspective view of the blower unit of FIG. 18 with a portion of the top cover removed to show internal details.
Figure 19:
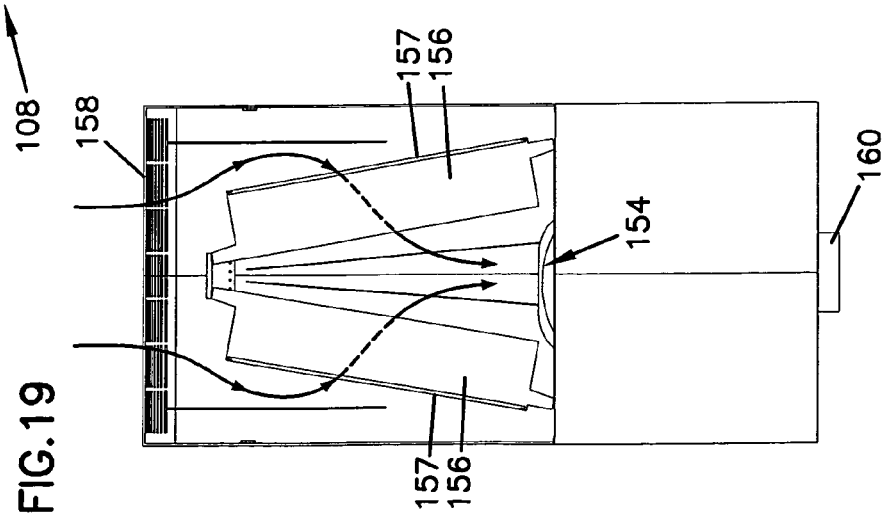
FIG. 19 is a top view of the blower unit of FIG. 18, with a portion of the top cover removed for clarity.

With reference to FIGS. 18–20, the blower unit 108 will now be described. The blower unit 108 comprises a two piece upper housing portion 150 that includes upper sections 151a, 151b and a lower housing portion 152 that together define a housing containing the fan 154, the fan motor, a pair of high efficiency filters 156, for example HEPA filters, for filtering air, and other elements necessary for operation of the blower unit 108. The fan motor is preferably a DC motor, which provides less heat introduction and is quieter than an AC motor. It is preferred that readily replaceable pre-filters 157 be positioned in front of the filters 156 in order to filter some of the contaminants out of the air flow prior to the air reaching the high efficiency filters 156. The pre-filters 157 are mounted to be replaceable at desired intervals, or when the pre-filters 157 become too dirty.

The blower unit 108 includes an air inlet 158 at one end, and an air outlet 160 at the other end. As illustrated in FIG. 19, the air entering through the inlet 158 is forced to undergo flow direction changes which helps to reduce the noise of the blower unit. The blower unit is preferably configured to have a height that allows it to be placed under most beds, although the blower unit can be located at other locations as well. The blower unit can also be provided with a number of controls, such as an on/off switch, speed controls, etc. In addition, the blower unit 108 can be provided with an indicator light to indicate that the pre-filters 157 need replacement.

Figure 21:
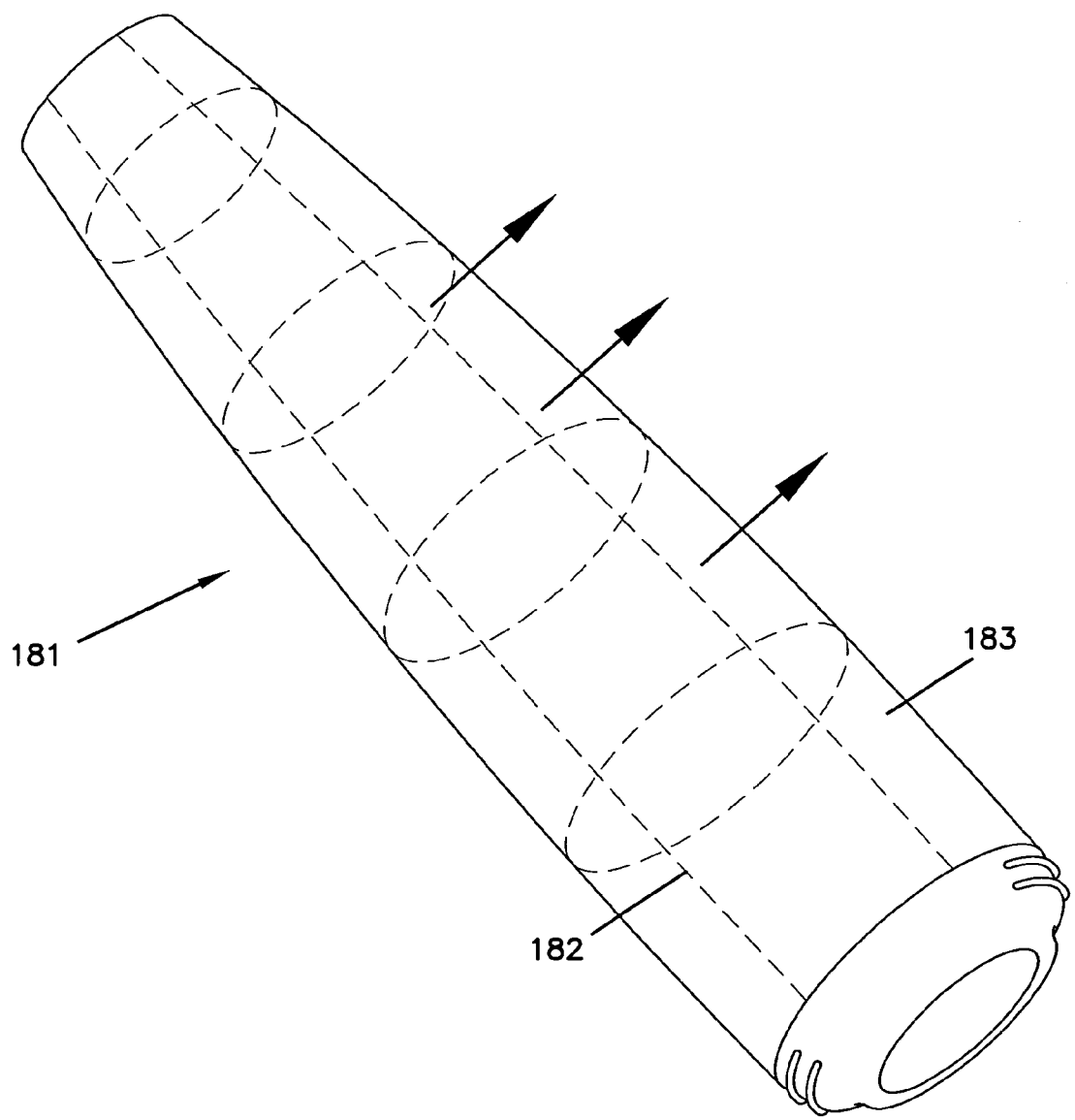
FIG. 21 is a view of another embodiment of an air delivery system.

FIG. 21 shows a configuration of a boom 181 that is to be cantilever mounted to a tower. The boom 181 is in the form of an open framework 182 (shown in dashed lines in FIG. 21) upon which a fabric sleeve 183 is disposed. The sleeve 183 is preferably removably disposed on the boom 181 to allow cleaning or replacement of the sleeve. A portion of the sleeve is made of porous fabric to allow discharge of air toward the bed as discussed above with respect to the boom 104. The porous portion preferably has generally the same extent as the outlet section 114 (e.g. extending over an arc of about 110 degrees). The remaining portion of the sleeve is preferably made of non-porous fabric.

Figure 16:
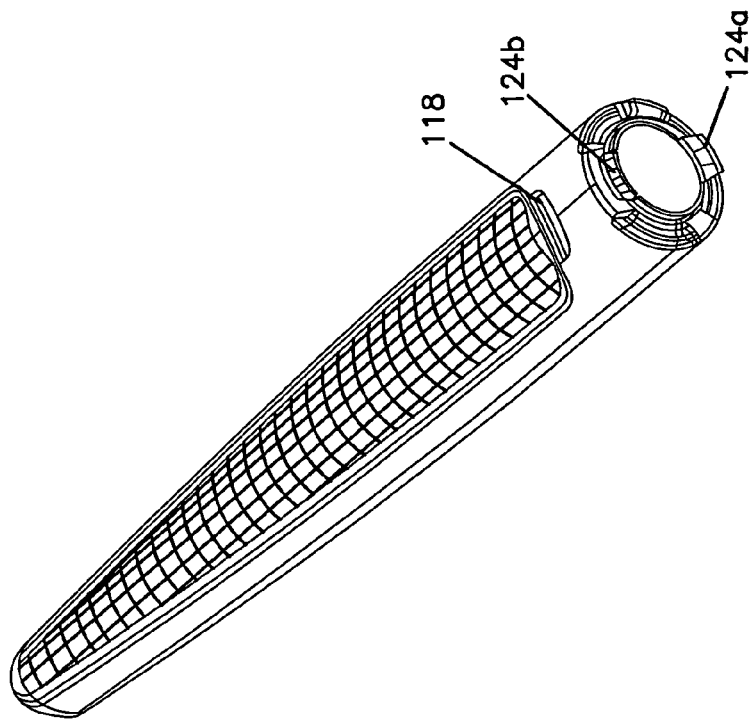
FIG. 16 is a detailed view of another embodiment of a delivery system, with the fabric cover removed to illustrate the grill.

With reference now to FIGS. 22A–22C, a pivotable, cantilever boom 184 is illustrated. The boom 184 can have a configuration as shown in FIGS. 11, 16 or 21, or another configuration. In this embodiment, the tower 186 includes a ball pivot 188 mounted at its upper end. The end of the boom 184 would be attached to the ball pivot 188 to allow the boom 184 to pivot between a stored position (shown in FIG. 22A) and a use position (shown in FIG. 22B). To accommodate the boom 184 when it is at the stored position, the tower 186 is recessed adjacent its upper end.

The ball pivot 188 is provided with a plurality of vent holes 190 and air openings to communicate the tower air passage with the interior of the boom 184. When the boom 184 is at the stored position shown in FIG. 22A, the vent holes 190 are exposed. At this position, the air from the blower unit can flow out the vent holes 190 into the room, so that the system acts as an air cleaner for the entire room. When the boom 184 is pivoted to the use position shown in FIG. 22B, the vent holes 190 of the ball pivot 188 pivot to a position where the vent holes are closed by the tower, and generally all of the air from the tower air passage is forced to flow into the boom 184.

FIGS. 23A–23C illustrate an embodiment of a detachable and stowable boom 192. The boom 192 can have a configuration as shown in FIGS. 11, 16 or 21, or another configuration. In this embodiment, the boom 192 can be detached from the tower 194 and stowed on the tower (as shown in FIG. 23A). For use, the boom 192 can be removed from it stowed position, and then attached to the tower (as shown in FIG. 23C). The tower 194 includes a recess 196 for receiving the boom 192 when it is stowed. Further, the top end of the tower 194 includes a first female attachment 198 and a second female attachment 200. The boom 192 includes a male attachment 202 adjacent its end that is configured to fit into the first female attachment 198 when the boom is stowed, and configured to fit into the second female attachment 200 when in its use position. The male attachment 202 can fit into the female attachments 198, 200 via a snap fit, a friction fit, or other type of connection that secures the boom 192 in its proper stowed and use positions.

In each of the embodiments, it is preferred that the conditioned air that is delivered by the delivery system to the breathing zone is at a minimum effective velocity in order to reduce any feeling of draftiness and minimize skin sensation. It is believed that an air velocity of between 15 and 100 feet per minute at the surface of the delivery system as the air exits the delivery system is acceptable.

The following table describes various airflow characteristics that are achieved using a boom, tower and blower unit such as that shown in FIGS. 11–13 and 18–20.

| Measurement | English Units | Si Units |
| --- | --- | --- |
| Overall volumetric flowrate | 55 cfm | 1.557 m³/min |
| Surface area of fabric face of air outlet section | 1.68 ft²/242 in² | 0.1561 m²/1561 cm² |
| Average velocity of air leaving fabric face of air outlet section | 33 ft/min | 10.06 m/min |
| Velocity of air 1 ft. away from air outlet section | 14.4 ft/min | 4.4 m/min |
| Air velocity range of air leaving fabric face: | | |
| Lower bound | 30 ft/min | 9.14 m/min |
| Upper bound | 60 ft/min | 18.28 m/min |
| Air temperature difference range: | | |
| Lower bound | −2 F | −1.11 C |
| Upper bound | +1 F | +0.56 C |

The last four entries in the above table are the upper and lower bounds of the air velocity leaving the fabric face and air temperature differences, which dictate the range of values in which a clean air envelope is properly created using the system in FIGS. 11–13 and 18–20. When the velocity of air leaving the fabric face is below 30 ft/min, external airflows from, e.g. home HVAC systems, can diminish the size of the clean air envelope. The upper end of the air velocity range is based on an airflow that would be strong enough to likely cause a person discomfort while sleeping. Since each person's discomfort level varies and is based on each person's opinion, the upper end of the air velocity range can vary. However, research has shown that an air velocity below 60 ft/min is virtually imperceptible and will not cause discomfort for most people.

Further, when used in a bedroom environment, the system 10 should be designed to be as quiet as possible. One way to reduce the noise level of the system is to design the conduit 16 to reduce noise. This concept is illustrated in FIG. 3, where the duct 30a includes a sound muffling section 31 composed of acoustically transparent fabric wrapped in sound absorptive material. The fabric can be, for example, a spun nylon or polyethylene material. The sound absorptive material can be, for example, a felt, wool or foam. Other fabrics and sound absorptive materials can be utilized as well.

The illustrated location of the sound muffling section 31 is exemplary only. Other locations for the section 31 are possible, including in the duct 30b and/or in the duct 30c. Further, more than one sound muffling section could be utilized.

Moreover, the use of a low noise blower unit 12 will further reduce noise levels.

In addition, the inventor has discovered that slight differences in the temperature of the delivered air can make a big difference in the size and shape of the clean air profile or envelope as it extends over the person's head and shoulders. In nearly every room there is a natural temperature gradient, with air near the floor being cooler than the air above it. Many bedrooms have a 1 to 4° F. difference above the bed to underneath the bed.

It has been found that the clean air envelope maintains an acceptable size and shape when the delivered air is not lower than the surrounding air by 2° F. and not higher than the surrounding air by 1° F. If the delivered air falls below this range, the height of the clear air envelope becomes too low. If the delivered air is higher than this range, then the air envelope tends to rise instead of sweeping horizontally over the user.

Figure 24:
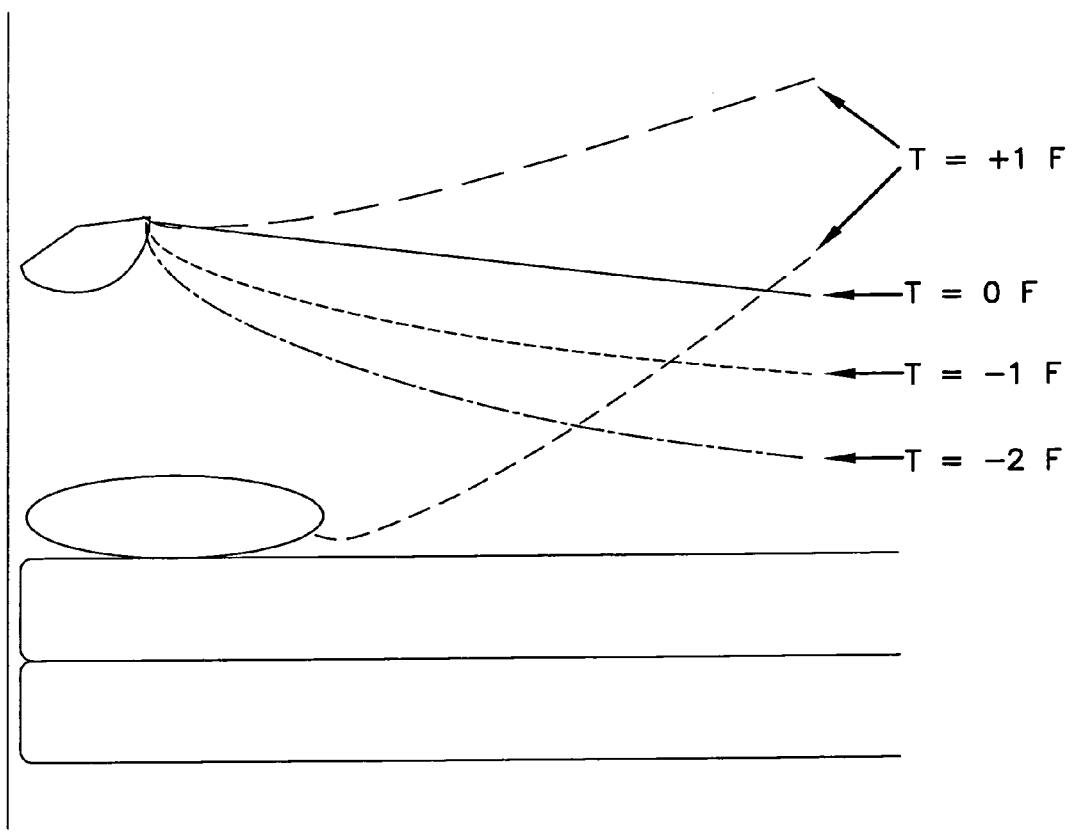
FIG. 24 is a diagram illustrating exemplary temperature conditions achieved utilizing the embodiment of FIG. 11.

A diagram illustrating various temperature conditions using the system in FIGS. 11–13 and 18–20 is illustrated in FIG. 24. The diagram is a side view of the system relative to the bed, with the bottom of the boom positioned approximately 17 inches above the surface of the bed, although the bottom of the boom can range from between about 16 inches and about 18 inches above the surface of the bed in accordance with the invention. The lines represent the boundaries separating the clean air envelope from the surrounding unpurified air at a specific air temperature difference. The upper and lower boundaries of the envelope that is formed when the difference in temperature between the air being delivered and the surrounding air is +1° F. are represented by dashed lines indicated by arrows. The upper boundaries of the envelopes that are formed when the difference in temperature is 0° F., −1° F. and −2° F., respectively, are also represented by lines indicated by arrows. For temperature differences of 0° F., −1° F. and −2° F., the lower boundary of each envelope is the surfaces of the mattress and pillow. The diagram shows that when the temperature of the air from the boom is decreased, thereby increasing the temperature difference between the boom air and the surrounding air, the height of the clean air envelope is decreased.

In the system, compression of the air by the blower unit can add upwards of 1° F. to the temperature of the delivered air, and if the motor of the blower unit is in the airstream, a 2 to 4° F. total increase in temperature can result. Depending upon the delivery system that is utilized, this increase in temperature can help or hurt the clean air envelope that is developed around the person's head and shoulders and the temperature increase needs to be accounted for. Therefore, the configuration of the air delivery system that is used will impact the air temperature considerations that must be accounted for to achieve optimal performance.

For a headboard delivery system, like the delivery system 24 shown in FIG. 2, it is believed that the temperature of the delivered air should be as close to the ambient temperature adjacent the delivery system as possible, ±2° F. Therefore, the motor used in the blower unit can be selected and designed to add some heat, for example a degree or two, to the air that is drawn in from the floor. By keeping the delivered air at a temperature close to ambient air temperature, the shape of the clean air envelope is optimized.

For a system that is designed with the delivery system located above and directing delivered air downward toward a person's head, for example the system 74 illustrated in FIG. 8, the blower unit and motor should be designed to add little or no heat to the air that is drawn in from the floor. As a result, the cooler floor air would be delivered above the person's head and move downward toward the person's head because the air is cooler than the surrounding ambient air. Movement of the cooler air toward the person will help to create the desired clean air envelope, and may reduce the horsepower requirements of the motor.

The above specification, examples and data provide a complete description of the manufacture and use of the invention. Since many embodiments of the invention can be made without departing from the spirit and scope of the invention, the invention resides in the claims hereinafter appended.

What is claimed is:

1. Apparatus for use in creating a zone of conditioned air over a surface of a bed, comprising:
   an air delivery unit having first and second ends, an interior air flow passage between the first and second ends, an air inlet opening in flow communication with the flow passage through which conditioned air enters the air flow passage, and an air outlet section that is configured to place the flow passage of the air delivery unit in flow communication with the exterior of the air delivery unit; wherein the air outlet section discharges airflow in a generally horizontal direction generally parallel to the surface of the bed, discharges airflow in a generally vertical direction generally perpendicular to the surface of the bed, and discharges airflow in back of the generally vertical direction for creating an air dam; and wherein the air outlet section extends over an arc angle of from about 110 degrees to about 130 degrees, with about 30 degrees to about 40 degrees of arc back of the vertical direction.

2. The apparatus of claim 1, wherein the arc angle is from about 120 degrees to about 130 degrees.

3. The apparatus of claim 2, wherein the air outlet section is configured to discharge conditioned air over an arc length of from about 7.0 inch to about 8.0 inch.

4. A method of creating a zone of conditioned air over a surface of a bed having a head end, comprising:
   providing an air delivery unit having first and second ends, a flow passage between the first and second ends, and an air inlet opening in flow communication with the flow passage, and an air outlet section that is configured to place the flow passage of the air delivery unit in flow communication with the exterior of the air delivery unit; and
   discharging the conditioned air from the air outlet section near the head end of the bed in a generally horizontal direction generally parallel to the surface of the bed and in a generally vertical direction generally perpendicular to the surface of the bed, and at a temperature that is not lower than the surrounding air by 2° F. and not higher than the surrounding air by 1° F.

5. The method of claim 4, further comprising discharging the conditioned air from the air outlet section with a velocity between about 30 ft/min and about 60 ft/min.

* * * * *